United States Patent [19]

Freeman et al.

[11] Patent Number: 5,183,761
[45] Date of Patent: Feb. 2, 1993

[54] METHOD OF MAKING CALIBRATION SOLUTION FOR VERIFYING CALIBRATION AND LINEARITY OF VERTICAL PHOTOMETERS

[76] Inventors: Mary J. Freeman; Gary M. Freeman, both of 1795 St. Andrews Dr., Palm City, Fla. 34990

[21] Appl. No.: 383,938

[22] Filed: Jul. 21, 1989

[51] Int. Cl.$^5$ .................... G01N 31/00; G01D 18/00; G12B 13/00
[52] U.S. Cl. .......................... 436/8; 436/19; 252/408.1; 250/252.1
[58] Field of Search ............... 252/408.1; 250/252.1; 436/8, 19

[56] References Cited

U.S. PATENT DOCUMENTS

| | | | |
|---|---|---|---|
| 3,997,470 | 12/1976 | Monte et al. | 436/8 |
| 4,056,485 | 11/1977 | Adolf et al. | 436/8 |
| 4,439,347 | 3/1984 | Sun et al. | 436/8 |
| 4,461,718 | 7/1984 | Kaye et al. | 436/8 |
| 4,615,972 | 10/1986 | Gallacher | 436/8 |

OTHER PUBLICATIONS

O. R. Fisher 1986 Catalog p. 1413 and p. 1053.

*Primary Examiner*—James C. Housel
*Assistant Examiner*—William Chan
*Attorney, Agent, or Firm*—Oldham, Oldham & Wilson Co.

[57] ABSTRACT

A method and device for calibrating or checking the calibration of vertical photometers. The invention may also provide easy and convenient assay results for diagnostic profiles. The invention comprises pre-dispensed amounts of a suitable reagent, chosen for the particular use, disposed in a vessel with an amount of a wetting agent to yield a reproducible meniscus in the resulting control solution. The control solution is dried to leave a precise amount of dried reagent and other constituents in the vessel which can then be stored and distributed until subsequent use. The dried control solution can then be reconstituted to provide a standard having known absorbance and physical characteristics.

9 Claims, 2 Drawing Sheets

METHOD OF MAKING CALIBRATION SOLUTION FOR VERIFYING CALIBRATION AND LINEARITY OF VERTICAL PHOTOMETERS

TECHNICAL FIELD

This invention relates to a means and method of verifying proper calibration and linearity of vertical photometers and providing controls and standards by which measurements can be easily and effectively obtained. More specifically, this invention relates to a method of verifying proper calibration and linearity of vertical photometers and providing control samples through the use of pre-dispensed, pre-calculated strips of a dry dyes or other control formula with a predictable final absorbance or other physical characteristic. This invention provides a more accurate, more convenient, and less technique-dependent means of verifying photometer calibration and providing control formulations than is currently available.

BACKGROUND OF THE INVENTION

The use of photometric measurements for clinical chemistry, immunology and microbiology are well known. In a horizontal photometer, a light beam is passed through an absorbing solution placed in a cuvette or other vessel with the beam entering the cuvette from one side, passing through the solution, and leaving the cuvette from the other side. The light beam enters the cuvette or other vessel at right angles to the vertical axis of the vessel. The horizontal measurement has been used in colorimetric and turbidity assays.

A vertical measurement may be accomplished using a vertical photometer wherein a vertical light path enters the cuvette from its bottom and passes through the solution to leave the cuvette from the surface of the solution or vice versa. With the vertical measurement, if the sample remains homogeneous and no evaporation of the solution occurs, the vertical and horizontal measurements are equivalent. As actual circumstances in the practical situation results in evaporation and inhomogeneity in the solution causing errors in the horizontal measurement which are not incurred with the vertical measurement technique. The vertical photometer may include a strip reader wherein a strip of microtiter wells will be consecutively read using a transport mechanism. Recently, the clinical assays used in the immunology and microbiology, have utilized enzyme immuno assays (EIA) which have been developed for many diseases including the AIDS HIV virus rather than the previously utilized agglutination assays. The EIA assays are more practically performed using microtiter volumes wherein the vertical photometer is especially useful. Thus, the use of microtiter wells and vertical photometers has grown significantly as even general chemistry applications are utilizing microwell strip or plate reading in order to use less reagent and thus reduce the cost per test.

The use of vertical photometers in clinical assays is therefore becoming quite important. These vertical photometers are calibrated and the calibrations verified by the manufacturer. However, it is both necessary and good practice to routinely monitor the performance of these instruments in the course of clinical practice and may in fact be required by regulatory agencies overseeing such practice.

Currently, a vertical photometer user is limited in the testing and verification methods available. The only commercially available methods involve reading through filters manufactured of glass or other materials. The filters used are usually neutral density filters which do not detect any chromophores or the concentration thereof as will be determined in clinical assay use of the photometer. The filters merely block a predetermined amount of light and pass a particular wavelength of light. The ability of the photometer to accurately detect light can therefore be tested with the use of neutral density filters, but the ability of the instrument to filter light or to detect light of a particular wavelength is not tested.

These techniques are further unrealistic as the photometric instrument is utilized to measure absolute absorbance of different fluids. The use of glass or other filters therefore does not account for several, variables which influence the final reading, under normal use of the instrument, such as: the chromophore of the fluid; the lens effect of the vessel in which the fluid is placed, meniscus effects of the liquid within the vessel, fluid effects or movement of a fluid in the vessel and other variables. Failure to account for or regulate these variables undoubtedly contributes to the variations observed and inaccurate results achieved by the instrument users presently. Remarkably, these variations are seen from one instrument manufacturer to another and even among different photometer models from the same manufacturer, even though all of these instruments are referenced to the same standard reference filters and substances provided by the National Bureau of Standards. It has also been found that the use of neutral density filters to check the linearity of a photometer will not yield any indication of whether the photometer will detect the chromophore.

The alternative to the currently available commercial methods of verifying calibrations is to attempt to utilize liquid dyes to simulate actual use in the laboratory. However, there are many problems with this method. Performing such a test is time-consuming, somewhat complex and allows for the introduction of many variables and errors.

Such a laboratory test to determine the accuracy of vertical photometer readings, would involve the use of the simple and well known Beers/Lambert Law which is stated as:

$$A = \log(I_o/I) = cl$$

where A is the absorbance, $I_o$ is the intensity of incident energy, I is the intensity of emergent energy, c is the concentration, 1 is the thickness of the absorber or path length, and is the molar absorbtivity constant for concentration in moles/liter. However, while applicable in theory, this law ignores the effects of surface tension by assuming that the liquid has a perfectly flat meniscus. Steps to compensate and correct for this are time consuming and complex as it would require physically measuring the path length and adding complex calculations not normally achievable by the user.

For example, in vertical reading using a fixed vessel size, such as a microtiter well, volume is proportional to path length and path length is proportional to absorbance. Therefore, slight pipetting variations from vessel to vessel or lab to lab will have significant effects on the results. This would then require a widening of the acceptable ranges, thereby decreasing the sensitivity of the dye in detecting miscalibrated instruments.

The surface shapes of different liquids also effects path length, which in turn effects absorbance. For example, water can have either a flat surface or a sloping surface in the microtiter well. Since the user must read through a small aperture to avoid light distorting effects of the vessel, these two differently shaped surfaces would produce different path lengths, thus different absorbance readings.

Packaging of pre-calculated dyes in liquid form would not be feasible, due to leakage problems and the inability to restore the volume of the liquid to the microtiter well in order to obtain a reproducible result. If liquid dyes were pre-dispensed and distributed as liquids, it would be found that an amount of the liquid dye would tend to remain on the exposed sides of the microwell and any cover which is placed thereover. Some variable amount of the path length from which an original absorbance measurement was obtained would be lost, and the original absorbance value would thus be in error. Alternatively, liquid dyes which were not pre-dispensed would require pipetting precision and protection from evaporation of the stock solutions for accurate results.

SUMMARY OF THE INVENTION

The present invention provides an easy and accurate method and means of calibrating or verifying the calibration of vertical photometers. The invention comprises pre-dispensed dye check strips which provide reproducible standards by which the functioning of the photometer can be ascertained. Each strip will contain a plurality of microtiter wells containing a dried dye material which when reconstituted according to performance specifications can be read in the various models of photometers and spectrophotometers to assess instrument performance. Users periodically testing their instruments with this system will be able to monitor the instruments linearity, calibration, filter integrity, repeatability, and lack of stray light.

The strips utilize pre-dispensed, evaporated dyes, which can be reconstituted with deionized water to yield a serial dilution of liquid dye solutions with predictable absorbance ratings. In one preferred form, this initial dye solution is produced from a reagent such as Para-Nitrophenol (PNP), along with an amount of sodium hydroxide, thimerosal and Triton X-100. The PNP is a stable dye solution which has a known peak absorbance at or near the wavelength to be tested. Sodium hydroxide serves to buffer the solution and thimerosal is added as a preservative. The Triton X-100 is a wetting agent. Sufficient amounts of Triton X-100 were added to produce a very deep, highly reproducible meniscus when distributed to the microwells. Serial dilutions of the dye are prepared by using an equally buffered, preserved and wetted diluent. The diluent becomes the blank and zero control.

The microstrip may be composed of 12 independent wells. Wells 1 and 12 are filled solely with diluent and serve as the blanks with well 1 being the blank and well 12 being the zero control. Wells 3 and 4 are filled with 1:8 dilution of the dye diluted with blank. Wells 2, 5 and 6 are filled with a 1:4 dilution of the dye with blank. Wells 7 and 8 are filled with a 1:2 dilution of the dye with the blank. Wells 9, 10, and 11 contain a 1:1 dilution of the dye with the blank. This distribution allows any error to be averaged and reduced along with providing accurate, absolute absorbance measurements and linearity verifications. Each strip is then left exposed to the air to evaporate. When complete, the wells contain precise and predictable amounts of dye, wetting agents, preservatives and buffer which adhere to the bottom of the plastic wells. In the dried condition, the strips may then be easily packaged and distributed to the user without adversely effecting the strips or their subsequent functioning.

When verification of the calibration of the photometer is desired, the strip may be reconstituted by adding 200 microliters of deionized water to each well. The strip is covered with laboratory film and left undisturbed for two hours. After the two hour period, each well contains a pre-determined dye solution with a predictable absorbance reading.

This microstrip system is much simpler and more predictable than serial dilutions done in the laboratory itself. Again, the Beers/Lambert Law states that Absorbance = molar absorbtivity constant X concentration X path length. The invention utilizes the fact that the absorbance will not change if the concentration and path length change inversely and proportionately. Therefore, since the chromophore is predispensed, relatively large errors in pipetting diluent will not affect the reading. A decrease in diluent volume would decrease the path length but cause corresponding increase in the solution's concentration, A similar error in pipetting dyes would, in contrast, decrease the path length but not cause the corresponding increase in concentration.

After reconstitution, the strip may then be inserted into the photometer. The strip is read in the single standard mode using an arbitrary value of as the concentration of the single standard material with 50 a wavelength of 405 nm with a 600 nm differential. The results can be immediately plotted on a chart to determine accuracy of calibration and to determine linearity. The calibration checking system of the invention makes a national standardization and criteria possible by such regulatory agencies as the CAP or NBS to provide uniform results from vertical photometric clinical assays nationwide.

Additionally, the system may comprise a predispensed amount of another reagent material such as a diagnostic complexing agent which when mixed with suitably prepared blood serum will react with a predetermined compound thereof so as to provide and produce assay results. For example, a lipid profile kit may be formed for the profile of the cholesterol, triglycerides, or HDL lipo proteins and other similar clinical diagnostic testing.

It is an object of the present invention to provide a means and method of calibrating and verifying calibration of vertical photometers which will improve the quality and reliability of vertical photometric reading.

It is another object of the present invention to provide verification of the calibration or assay results for a vertical photometer by the use of dye dilutions or other reagents which have been verified on a reference instrument.

It is a further object of the present invention to provide a means and method of calibrating and verifying photometers which will be accurate despite pipetting errors which may occur during reconstitution of dried dye dilutions.

It is yet another object of the present invention to provide a means and method of calibrating and verifying photometers which can monitor the linearity, calibration, filter integrity, repeatability and lack of stray light of such photometers.

It is an object of the present invention to provide a means of calibrating and verifying photometers which can be pre-packaged and pre-calculated by the manufacturer for the convenience and simplicity of the user.

BRIEF DESCRIPTION OF THE DRAWINGS

These and other objects and advantages of the present invention will become more readily apparent from the more detailed description of preferred embodiments taken in conjunction with the drawings, wherein.

DETAILED DESCRIPTION OF THE INVENTION

Figure 1:
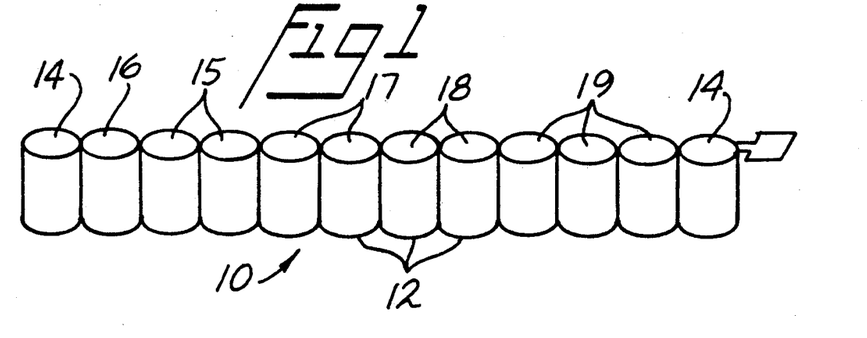
FIG. 1 shows a test strip for the kit of the present invention including a series of microtiter wells having pre-dispensed dried control solutions disposed therein.

With reference to FIG. 1, the kit 10 enabling verification or determination of the calibration and linearity of a vertical photometer is shown. The kit 10 comprises a plurality of containers or vessels 12 which may be microtiter wells having a predetermined volume in which an amount of a desired control solution may be placed. Serial dilutions of the solution are selectively placed in several of the microtiter wells 12 as will be hereinafter described so as to average any error incurred in measurements due to pipetting errors upon reconstitution of a dried control solution. In a preferred example, a working dye solution is produced to be highly absorbing, having a peak absorbance at or near the wavelength at which testing is desired. The wavelength can be chosen to correspond to a particular assay material for which the photometer is to be used to check calibration and linearity of the photometer for a predetermined wavelength and a range around this wavelength.

Figure 2:
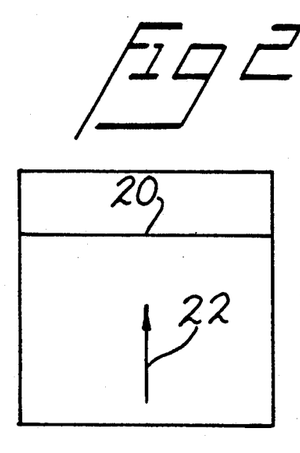
FIG. 2 and FIG. 2A show enlarged side views of a microtiter well as used in the test strip of FIG. 1 showing common variable surface characteristics of a control solution in the well.
Figure 2A:
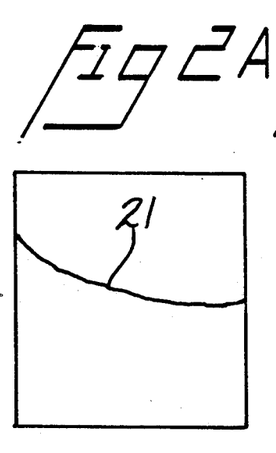
Figure 3:
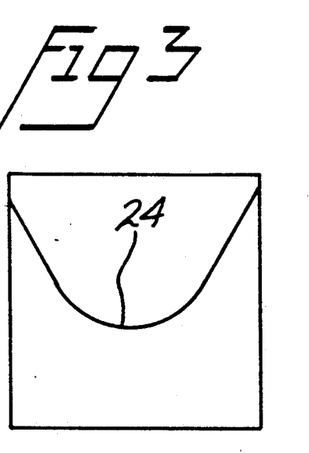
FIG. 3 shows the surface characteristics of the prepared control solution of the invention wherein a wetting agent is provided to form a reproducible meniscus.

The dye solution may be buffered and preserved for stability of absorption qualities over a period of time so as to be useful to the user for periodic checking and verification of the photometers performance. A considerable amount of wetting agent may be utilized to give the dye solution a very deep and highly reproducible meniscus which may be termed as "slippery" when dispensed in the microtiter wells. As seen in FIGS. 2, 2A and 3, the meniscus of the dye solution without a wetting agent included may take the shape as shown in FIGS. 2 and 2A at 20 and 21 or some other shape randomly and a particular shape is not readily reproducible. A variable meniscus will effect the absorption reading gained from this sample according to the Beer/-Lambert law as stated previously. It is known that different liquids have different shaped surfaces when disposed in a container such as a microtiter well which can effect path length of the light through the sample in a vertical photometer. Water, for example, can have flat surface or may retain a sloping surface in a microtiter well according to the surface tension characteristics thereof. Similarly, other liquids will behave according to the surface tension of the liquid and will similarly effect absorption readings using a vertical photometer.

By the use of a fixed vessel size such as a standard microtiter well, the volume will be proportional to the path length when using a vertical photometer. This should be evident in that the vertical photometer measures absorption along a path as shown by arrow 22 wherein the path length can vary according to the surface characteristics of the liquid being measured. It is also a function of the vertical photometer that the readers must read through a small aperture so as to avoid seeing scatter or other light-distorting effects of the vessel in which the liquid is placed. The particular surface shape will thus have a significant effect upon the path length and therefore the absorbance reading in the photometer. Using a wetting agent in the stable liquid dye of the present invention allows the very deep and highly reproducible meniscus as shown in FIG. 3 at 24 allowing use of the dyes in the verification and calibration testing. Thus, the use of a wetting agent will uniformingly yield the meniscus as shown in FIG. 3 or some other reproducible shape upon reconstitution of a dry control solution. It is also found that beading of the control solution of the microwell walls is also far less likely to occur than if no wetting agent was utilized. Such testing can be conducted by a user without significant error being incurred based upon meniscus effects. The deep meniscus obtained by using the wetting agent in the control solution as shown in FIG. 3 will thus provide a more accurate check consistently. A meniscus as shaped in FIG. 3 also will help detect if the transport mechanism on the strip reader of the vertical photometer is not properly aligned by indicating increasing absorbance as you read further and further from the well centers or the shortest path length.

Serial dilutions of the dye are then prepared with the basic diluent becoming the blank from which dilutions are made. The serial dilutions are then uniformly dispensed into the microtiter wells 12 of the strip 10 to form a plurality of wells having different absorbance characteristics wherein the absolute absorbance readings will verify calibration of the photometer and the relationship of the absorbance readings gained from the serial dilutions will yield an indication of linearity of the photometer.

In the preferred example as shown in FIG. 1, there are provided twelve microtiter wells 12 each having an amount of dye solution or blank diluent dispensed therein. A working dye solution formed from a precise dilution of a concentrated dye is used to form a base from which serial dilutions are prepared. The serial dilutions are prepared by diluting the working dye with an amount of a blank which when mixed with a dye will yield desired physical characteristics for the resulting liquid in the vessel. In the first and last microtiter wells 12 are dispensed an amount of the blank as indicated at 14 without any of the working dye and simply being the diluent used to form the serial dilutions of the working dye. The measurements gained from the blank in the first well gives a reference for zero absorbance and the last well can then be used to determine if any drift or tailing effect from a misaligned transport mechanism is seen. A 1:4 dilution of the working dye is then prepared and dispensed in the well as shown at 16 for use as a reference for determining calibration of the instrument.

A 1:8 serial dilution is then dispensed in wells as shown at 15, along with additional 1:4 dilutions in wells as shown at 17, and 1:2 dilutions in wells as shown at 18. Three wells have dispensed therein 1:1 dilutions of the working dye solution as shown at 19 to form a series of serial dilutions from which subsequent linearity determinations can be made for the particular instrument being checked.

By providing a plurality of wells for each of the serial dilutions as well as the working dye. solution, any small error which may be incurred due to non-uniformities in the preparation thereof will be averaged and limited. Additionally, the repeatability of the instrument can be checked. It is of course recognized that various other vessel arrangements may be utilized to accomplish the desired goals of determining absolute absorbance and relative concentration measurements for a series of dye solutions having known absorbance characteristics with which the photometer measurements can be compared. It should also be recognized that the test strip in addition to yielding an initial calibration determined by the absorbance of the dye in the microtiter well as shown at 16 and the linearity determine by the relationship of the 1:4 dilution of the dye and the other three dilutions, allow filter integrity, and an indication of stray light effects for the instrument. By conducting a plurality of tests over time on the photometer, continued calibration accuracy will imply filter integrity of the device. Also filter 1 deterioration in the photometer may result in a loss of linearity at the high end of absorbance measurements indicating stray light effects which can be determined by comparison of the serial dilutions in the strip.

Preparation of the test strip in the manner described above using a vessel, such as a microtiter well or similar container, can be used with microtiter plate readers since the strip will fit into a strip tray which can be loaded and read utilizing the photometer. The dispensed dyes are then left exposed to the air to evaporate or may be dried to quicken the evaporation process. After dehydration, the vessels will contain precisely the correct amounts of dried , dyes or other reagents, wetting agents, preservatives, and buffer salts which may be used in their preparation to form a residue which adheres well to the bottom of the vessel and is thus easily distributable without error being incurred due to loss of the reagent and other materials. Reference absorbance values for the prepared control solution are then obtained by measuring the path length and measured absorbance of the dilutions with their unique surface and absorption characteristics. Utilizing precision vernier calipers at the center of the well where the reading of the vertical photometer will be conducted, the path length is very precisely measured for calculation of absorbance. The path length measurements of many wells which yield equal absorbance readings are averaged to improve the accuracy of this measurement. The absorbance of the working dye along with the serial dilutions are then read on a spectrophotometer which is referenced to NBS standards to obtain reference absorbance values for a particular batch of the working dye. The absorbance values are multiplied by the path length correction factor as measured with the calipers to obtain the expected absorbance values for the dyes at a predetermined path length.

The dried or dehydrated dye solutions used in the test strip may be then distributed to the user to be used for the checking of a vertical photometer at various intervals over a period of time. The user may reconstitute the dried dissolutions in-situ when testing of the photometer is to be conducted. It has been found in accordance with a re-stated formulation of the Beer-Lambert Law, which states that $A = (a/s) m$ where, $A$ = absorbance
$a$ = specific absorbance
$s$ = cross-sectional area of the vessel
$m$ = mass of the absorbing substance, that the total mass of the absorbing substance will always be contained within the limits of the vessel and will be independent of the vertical distribution and amount of solvent within the vessel. Thus, absorbance will not change if both concentration and path length are allowed to change inversely and proportionally. If evaporation of the dye solutions as prepared in the test strip of the present invention is allowed. The lost volume will consequently result in shorter path length, but absorbance will remain substantially constant due to the increase in concentration of the absorbing material within the dye solution proportionally.

Thus, for the vertical photometric measurement, the test strip of the present invention of dried dye dilutions may be reconstituted by adding an amount of an activator, such as de-ionized water, to each well. It is desirable that a somewhat precise amount of the activator be pipetted into the vessel, but in accordance with the above principal, pipetting errors of up to 10 percent may have no effect upon the resultant absorbance measurements taken. Such pipetting errors would be intolerable if the user were to try and prepare serial dilutions for use in calibration and linearity studies. The variations seen from lab to lab or well to well in the microtiter strip which may require spurious widening of acceptance ranges and thereby reduce sensitivity of the dye for the detection of mis-calibrated instruments is therefore overcome. It should also be recognized that although very small volumes of the dye solutions are utilized, errors in the pipetted amount of activator when reconstituting will not have significant detrimental effects in resulting absorbance measurements. Additionally, the standard theories underlying absorbtivity are based upon having a perfectly flat meniscus which in a realistic sense cannot be achieved consistently. With the test strips of the present invention, the chromophore of the dye solutions is appropriately pre-dispensed such that the concentration thereof will vary inversely and proportionally with the path length changes which may be incurred.

In the reconstitution of the test strips, after an amount of an activator such as de-ionized water is added to the dried dye dilutions, the strips may then be covered with a laboratory film to prevent any significant evaporation of the reconstituted solutions. The reconstituted strips are given an opportunity to accomplish mixing over a waiting period so as to obtain uniform dye distributions in the vessels. A mixer may be utilized to speed up the preparation of uniformly distributed dye dilutions if desired. Once uniform and homogeneous dye dilutions are obtained, readings may be taken for each of the vessels and the absorbance observed will be compared to the assigned or expected results issued by the manufacturer. To facilitate proper reduction of the observed absorbance readings, pre-calculated ranges for every point or each serial dilution may be provided in accordance with FIGS. 4 and 5. The plots enable the results to be easily plotted for instant visual determinations of whether the tested photometric instrument meets the acceptance criteria for calibration, linearity and repeatability. Alternatively, the user may simply take the observed absorbance readings to develop absorbance ratios with the assigned or expected results for the serial dye dilutions, and thereby make the determination of whether the test instrument falls within the accepted range of accuracy.

Figure 4:
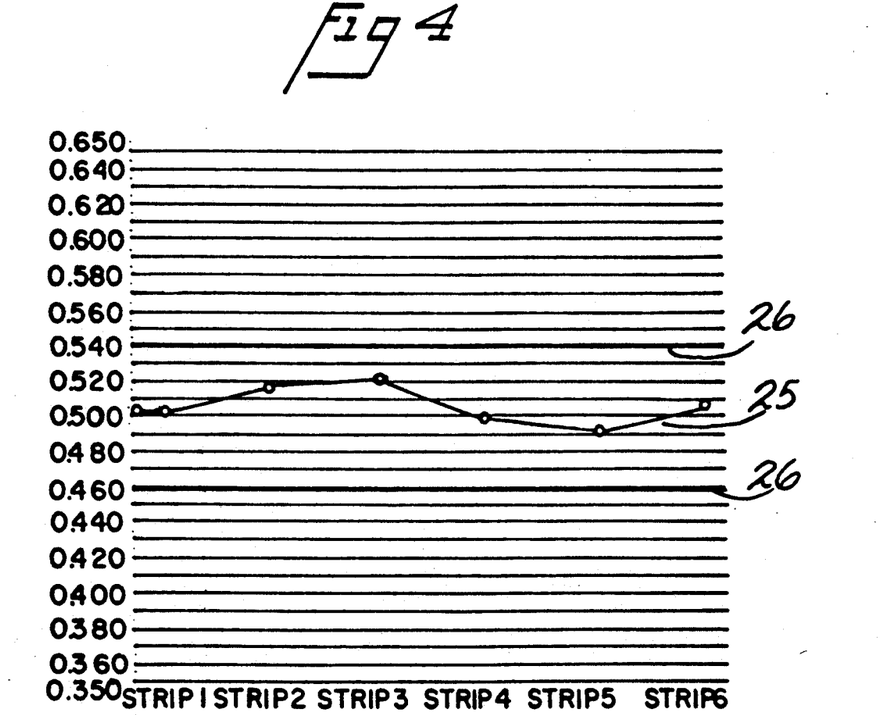
FIG. 4 shows a calibration plot indicating calibration within acceptable limits conducted over a period of time.
Figure 5:
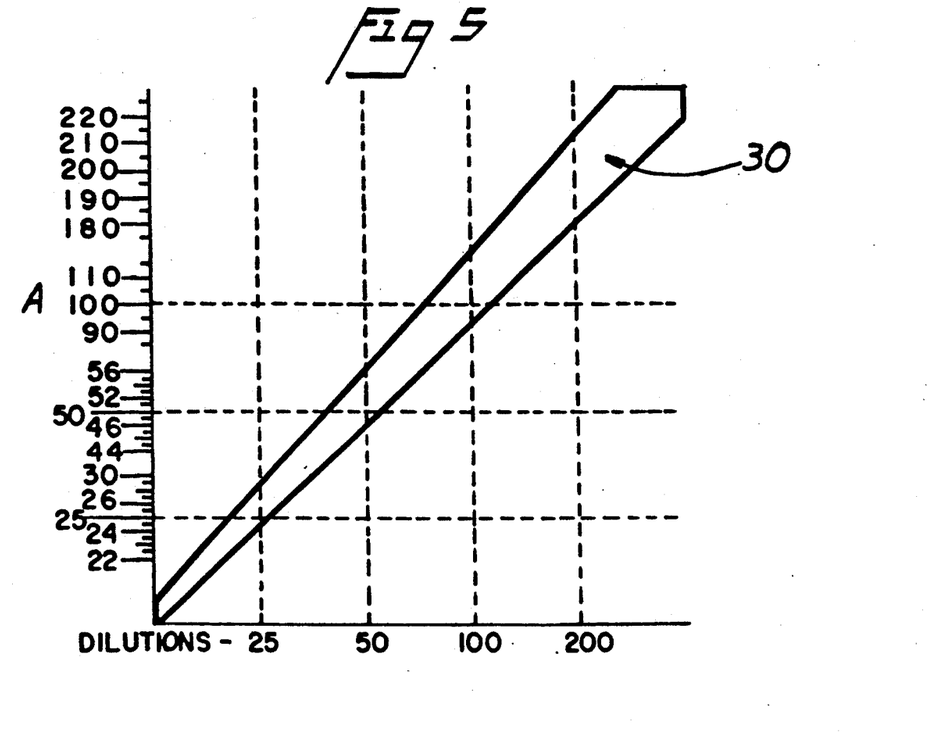
FIG. 5 shows a linearity plot on which absorbance readings may be immediately plotted and the linearity determined therefrom.

More specifically referring to FIGS. 4 and 5, a calibration record and linearity plot are shown respectively. The calibration record utilizes initial observed absorbance measurements of the 1:4 dilution of the working dye with a proper amoung of diluent. The observed absorbance is plotted on the calibration record as shown at 25 and a range around the observed reading such as plus or minus 0.040 absorbance units as shown by lines 26 becomes the acceptable range for the particular instrument being tested. The particular absorbance readings at 25 and the acceptable range at 26 for calibration will be determined by the instrument manufacturer, and will also based upon the original: instrument specifications of each instrument. The initial absorbance of the observed measurement should be within the range provided for the instrument model being utilized, and if so will indicate acceptable calibration as compared to an NBS standard reference. Subsequent absorbance readings should also be within the range determined from a first measurement indicating that the no significant change in calibration has occurred with time in the instrument tested.

In FIG. 5, the linearity plot utilizes absorbance measurements of the serial dilutions of the dye wherein the average of the concentration readings for the 1:8 dilution, the 1:4 dilution, the 1:2 dilution, and the 1:1 dilution will be plotted against the known values according to the predispensed serial dilutions referenced against and NBS standard. An acceptable range is provided as shown at 30 and points lying within this range indicate accurate linearity of the instrument being tested. An indication of stray light effects may also be seen in the linearity plot by a loss of linearity in the high end indicating aging of the filter in the instrument and lack of filter integrity. It should also be recognized that by observing absorbance readings for a plurality of individual serial dilutions, the repeatability for each measurement can be determined by taking the difference in absorbance between the two or more readings. The difference in absorbance between the readings for the same serial dilutions should not differ by more than a specified amount indicating acceptable repeatability.

It should be evident from the foregoing that the test strips of the invention, when dried or dehydrated, allow a strip of microtiter wells or other vessels to be packaged for reliable and cost effective distribution of the kit without the inherent problems associated with microtiter wells. Due to the fragile construction of the microtiter wells, as well as spillage and leakage problems of dispensed liquids, it has not been feasible to pre-dispense liquids from a single pipetting source into strips or plates for distribution as a calibration checking and testing kit. The invention allows a precise pre-dispensed amount of a predetermined dye solution and serial dilutions thereof to be effectively distributed to a user for accurate calibration determinations on individual photometric instruments. The dry dye system has a predictable final absorbance referenced to a NBS standard and offers convenience and simplicity for the user as computations and acceptance criteria has been carried out before distribution to the user. The dry dyes can be reconstituted with water without requiring pipetting precision, and the system incorporates all the conditions of the true reading situation lacking in prior art techniques. The invention can be utilized for improved standardization of vertical photometric readings and could also be used by manufacturers to set new instruments to specified values for future calibration verification. The reconstituted dilutions of the dye allow verification of appropriate performance specifications over the entire operating range of a particular instrument tested thereby assuring quality and reliability in vertical photometric measurements.

As previously described, substantially the same techniques can be utilized for preparing and producing assay results. As an example, a lipid profile kit may contain a dried diagnostic complexing reagent chosen to react specifically with a compound in blood serum or other patient serum to yield assay results. The kit would also comprise controls and standards such that the assay results can be referenced to known standards and will give proper and accurate readings of the particular profile being sought. In use, a patient's serum may be diluted with a buffer provided with the kit. The buffer and patient serum become a diluent which is then dispensed into the microtiter wells containing the dried reagent or control solution. Upon dispensing of the diluent into the microtiter wells, the diagnostic complexing agent which is the reagent will react with the patient serum and produce assay results. For example, a lipid profile may be developed for monitoring the level of cholesterol, triglycerides, HDL in the serum. Other profiles such as cardiac, liver or kidney profiles are common. The diagnostic complexing reagents which may be utilized in these profiles are well known and these conventional reagents can be incorporated with the method and apparatus of the invention.

EXAMPLES

This invention will now further described in detail with reference to the specific examples that follow. It will be understood that these examples are by way of illustration of the invention and not by way of limitation of the scope thereof.

A base dye solution was prepared using paranitrophenyl phosphate (PNP) being common with use of EIA development. This concentrated PNP solution was precisely diluted using 1:2 with the solution of 1M Sodium Hydroxide utilized as a buffer, Thimerosal which is a common preservative and an amount of Triton X-100 which is a wetting agent and surfactant forming a desired and reproducible meniscus in the resulting solution. Other wetting agents may be used such as polyvinyl alcohols as long as a reproducible meniscus is formed. The base material was stored at 4° C. and provides a stable dye solution which has a peak absorbance at or near a predetermined wavelength of light.

EXAMPLE 1

This example illustrates the preparation of a series of serial dilutions being prepared in the manner of the invention as previously described to demonstrate substantially equivalence of the reconstituted dye solutions with freshly prepared serial dilutions of similarly prepared dye solutions.

A test strip was made in accordance with the invention by pipetting the working PNP dye solution into Immulon flat bottom removawells manufactured by Dynatech Labortories, Inc. The individual wells of the strip had dispensed therein a blank of the diluent constituting 200 microliter of the alkaline buffer material, wetting agent and preservative. Serial dilutions of 1:8, 1:4, and 1:2 along with the working PNP solution was then dispensed in 200 microliter portions into the microtiter wells as described with reference to FIG. 1. The prepared test strips were read to establish "fresh" states and then allowed to evaporate forming the dried dye residue including buffer, wetting agent and preservative. Over a period of 12 weeks, a strip prepared in this fashion was reconstituted with 200 microliter of de-ionized water and allowed to sit for two hours for thorough mixing. Similarly prepared fresh serial dilutions of PNP were prepared in order to check reconstituted measurements against freshly prepared samples. Using a photometer referenced to NBS standards, the following results were found and are given in Table 1. The strip was read in the single standard mode using a standard value of 50. The wavelength at which measurements were conducted was in range of 405–600 nm for the PNP solution.

TABLE 1

Equivalence of Reconstituted Dyes and Fresh

| well # | n= | mean absorbance fresh | mean absorbance dried | coefficient of variation fresh | coefficient of variation dried | % deviation from fresh |
|---|---|---|---|---|---|---|
| 3 | 16 | 0.272 | 0.271 | 0.69% | 1.29% | (−)0.37% |
| 5 | 16 | 0.547 | 0.551 | 1.51% | 2.27% | (+)0.73% |
| 7 | 16 | 1.084 | 1.093 | 0.92% | 1.28% | (+)0.83% |
| 9 | 16 | 1.915 | 1.926 | 0.58% | 1.00% | (+)0.57% |

It is noted that the increase in percent of the coefficient variation from the fresh to the dried may be attributed to the fact that the strips were reconstituted on different days using different lab technicians, measuring devices and environmental conditions as well as other variables. The fresh readings were made on the same day wherein only one component of variation in the fresh readings constituted the strip itself. Regardless of the other variables which may have affected the experiment, acceptable variation and equivalent mean values were demonstrated for the reconstituted strips.

EXAMPLE 2

Figure 6:
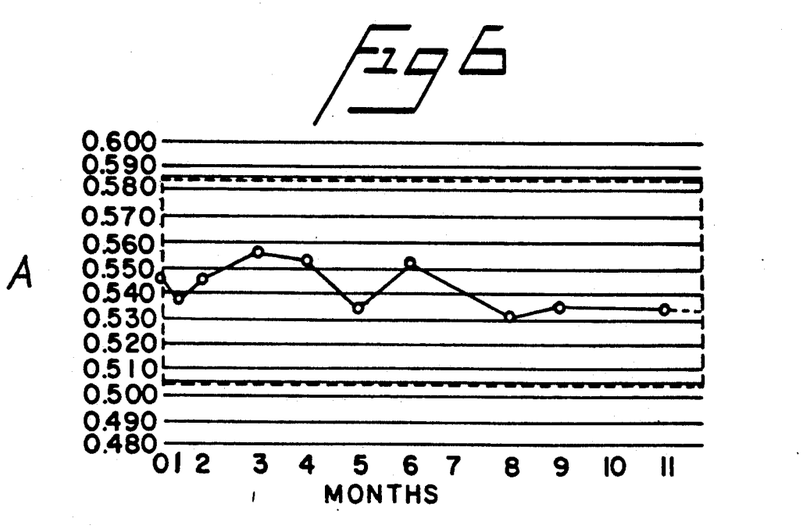
FIG. 6 shows absorbance measurements in a test over a period of time.

Using a plurality of the test strips as prepared according to Example 1, the individual wells of the strip were reconstituted monthly and read using a Sigma EIAminilab photometer being referenced to NBS Standards. Values obtained from the reconstituted test strips were compared to initial reference values for the serial dilutions to determine the shelf life of the dried dye solutions. The results are shown in FIG. 6, and it can be seen that there was no significant difference between the results obtained over an 11 month period of time and the initial values. The calibration plot as shown in FIG. 6 was determined by averaging the absorbance from the 1:4 serial dilution of the working PNP with the blank. Month zero as shown in the plot is the mean absorbance of the freshly prepared serial dilutions. The specific absorbance measurements are shown as follows n Table 2.

TABLE 2

Life of Dried Dye Solutions

| months stored | ave abs. | change from baseline |
|---|---|---|
| 0 | 0.547 | — |
| 1 | 0.539 | (−) 1.5% |
| 2 | 0.547 | 0.0% |
| 3 | 0.557 | (+) 1.8% |

TABLE 2-continued

Life of Dried Dye Solutions

| months stored | ave abs. | change from baseline |
|---|---|---|
| 4 | 0.553 | (+) 0.7% |
| 5 | 0.537 | (−) 1.8% |
| 6 | 0.550 | (+) 0.5% |
| 7 | | |
| 8 | 0.532 | (−) 2.7% |
| 9 | 0.537 | (−) 1.8% |
| 10 | | |
| 11 | 0.533 | (−) 2.6% |

Similarly, linearity was checked on each of the monthly reconstituted strips wherein an accepted range was determined to be plus or minus 10 percent of the mean concentration values calculated from the freshly prepared working PNP having a mean concentration of 25. Table 3 shows the linearity results for the reconstituted strips over time as being within the 10% acceptance range.

TABLE 3

Linearity of Reconstituted Samples With Time

| | Serial dilutions | | |
|---|---|---|---|
| months stored | 1:8 24.8 (22.3–27.3) | 1:4 99.5 (89.6–109.5) | 1:2 176 (158–194) |
| 1 | 24.7 | 99.9 | 176 |
| 2 | 24.7 | 99.0 | 174 |
| 3 | 24.7 | 99.6 | 173 |
| 4 | 24.2 | 101 | 177 |
| 5 | 24.3 | 101 | 176 |
| 6 | 24.0 | 100 | 176 |
| 7 | | | |
| 8 | 24.6 | 99.6 | 174 |
| 9 | 24.6 | 99.7 | 175 |
| 10 | | | |
| 11 | 23.7 | 99.4 | 170 |

EXAMPLE 3

The reduced impact of pipetting error was demonstrated by filling 10 test strips with 200 microliters of the blank diluent in one well and 11 wells of 1:4 PNP dilution. The prepared strips were evaporated and subsequently reconstituted with variable volumes of activator being de-ionized water. Table 4 shows the results of imprecise pipe heading during the reconstitution step and its affects upon the resulted absorbance measurements.

TABLE 4

Indication of Pipetting Errors

| recon. volume | n= | mean abs. | C.V. | deviation from 200 ul |
|---|---|---|---|---|
| 200 μl | 22 | 0.465 | 1.1% | (control) |
| 170 μl | 11 | 0.452 | 1.1% | (−)2.8% |
| 180 μl | 11 | 0.456 | 0.9% | (−)1.9% |
| 190 μl | 11 | 0.457 | 0.6% | (−)1.7% |
| 195 μl | 11 | 0.461 | 1.1% | (−)0.9% |
| 205 μl | 11 | 0.464 | 0.6% | (−)0.2% |
| 210 μl | 11 | 0.471 | 0.7% | (+)1.3% |
| 220 μl | 11 | 0.469 | 0.7% | (+)0.9% |
| 230 μl | 11 | 0.480 | 1.3% | (+)3.2% |

In Table 4-A, the control is demonstrated by pipetting into a test strip a blank of the diluent and varying volumes of 1:4 dilution of the working PNP. The absorbance of the individual wells were then read in the photometer and the expected variation corresponding to changes of volume and concentration are shown.

TABLE 4A

Variation of Absorbance with Volume of Working Dye

| pipetted volume absorbance ul 0.482 | absorbance (control) | volume (control) |
|---|---|---|
| 170 μl 0.413 | (−)15.0% | (−)14.3% |
| 180 μl 0.434 | (−)10.0% | (−)10.0% |
| 190 μl 0.460 | (−) 5.0% | (−) 4.7% |
| 195 μl 0.472 | (−) 2.5% | (−) 2.1% |
| 205 μl 0.496 | (+) 2.5% | (+) 2.9% |
| 210 μl 0.508 | (+) 5.0% | (+) 5.4% |
| 220 μl 0.535 | (+)10.0% | (+)11.0% |
| 230 μl 0.565 | (+)15.0% | (+)17.2% |

Although the examples shown use the stable PNP dye solution, the invention contemplates other stable dye solutions for different wavelengths of light and to check the calibration of the photometer at such wavelengths. For example, at a wavelength at or about 340 nm., a dye solution comprising an amount of potassium dichromate along with an amount of 0.1% sodium hydroxide or other alkaline buffering agent and an amount of 0.01% Triton X-100 as the wetting agent and 0.2% sodium azide acting as a preservative may be used. Federal food dyes such as yellow dye #2 or red dye #40 may be utilized with neutral non-tris buffers, a wetting agent such as Triton X and preservatives for studies at a wavelengths at or about 450 nm and 492 nm respectively. It is also been found that at a wavelength of 492 to 520 nm, a cobaltic sulfate in 0.1% sodium hydroxide with 0.01% triton X-100 and 0.2% sodium azide may be suitable. Other reagents which may be useful are nickel sulfate or chromic perchlorate in a sulfric acid to keep the metals from precipitating to form reagents for calibration at 550 and 600 nm. With these last mentioned control solutions, a dispersant may be necessary to help re-dissolve reagent and buffer salts introduced into the control solution. It should be evident that these and other particular control solutions can be dried and reconstituted to provide the novel features of the invention.

The preceding examples show that the reconstituted dried dye solutions result in a non technique-dependent device comprising a pre-dispensed and pre-calculated system. The system is simply and conveniently used by an instrument user to monitor instrument performance. The calibration, linearity, filter integrity, repeatability and lack of stray light can be demonstrated with a system which incorporates all the conditions of the true reading situation in vertical photometry. The pre-dispensed, evaporated dies can be reconstituted with water without requiring pipetting precision, and allow accurate results to be obtained. Although the invention has been described with reference to specific embodiments thereof, it should be apparent that various changes and modifications will be suggested to one skilled in the art and it is intended to encompass such changes and modifications as fall within the scope of the appended claims.

What is claimed is:

1. A method of making a test kit to be used for taking vertical photometric measurements comprising:
    (1) providing a control solution having at least one reagent and a wetting agent therein, provided in at least one vessel, said control solution having predetermined and predictable physical characteristics, said wetting agent forming a predetermined meniscus within said vessel,
    (2) drying said solution to obtain a dried residue within said vessel having a pre-dispensed amount of said reagent, wherein said dried residue may be stored for subsequent use,
    (3) reconstituting said dried residue using an amount of an activator to reform said control solution such that said reformed control solution will have substantially equivalent physical characteristics to said control solution provided in step one, including substantially reforming said predetermined meniscus in said vessel, such that said reformed control solution may be used to obtain accurate measurements based upon the pre-dispensed amount of said reagent.

2. A method as in claim 1, wherein,
said at least one reagent comprises a stable dye solution including an amount of a dye having a preselected chromophore and having a known absorbance in a range about a predetermined wavelength of light used in vertical photometric measurements.

3. A method as in claim 1 further comprising providing,
said pre-dispensed reagent comprising a diagnostic complexing agent which will react specifically with a predetermined compound within said activator utilized to reconstitute said residue so as to produce and yield assay results measured with a vertical photometer.

4. A method as in claim 1, wherein,
said vessel is a microtiter well and a plurality of said wells are provided with differing concentrations of said reagent disposed therein so as to obtain variable measurements proportional to the amount of said reagent in said reconstituted control solution.

5. A method as in claim 1, wherein,
said reagent comprises a dye selected from the group consisting of para-nitrophenol, potassium dichromate, yellow dye #2, red dye #40, cobaltic sulfate, nickel sulfate and chromic perchlorate to provide stable dye solutions yeilding reproducible absorbance measurements at predetermined wavelengths of light using a vertical photometer.

6. A method as in claim 1, further comprising providing,
said control solution further including an amount of a buffering agent, and preservatives.

7. A method as in claim 1, wherein,
said activator is de-ionized water wherein an amount of said water is measured and disposed in said vessel to reconstitute said dry residue, with said physical characteristics not being dependent upon the amount of activator used in the step of reconstituting said dried residue.

8. A method as in claim 1, wherein,
said amount of said activator used to reconstitute said dried residue is blood serum from a patient diluted with an amount of a buffer forming a diluent wherein a predetermined amount of said diluent is disposed into said vessel to reconstitute said dried residue and react with said reagent to produce as a result.

9. A method of making an apparatus for calibration of and determination of the linearity of a vertical photometer comprising the steps of:
providing a stable liquid dye solution having a known absorbance value and predetermined physical characteristics, said solution including an amount of a wetting agent, placing predetermined amounts of said dye solution in separate vessels of predetermined volume, said wetting agent in said solution acting to produce a predetermined meniscus within said vessels, drying said amount of said liquid dye solution to form dehydrated dyes in said vessels which may be reconstituted utilizing an activator liquid so as to have substantially similar physical characteristics including said predetermined meniscus within said vessels and known absorbance values such that measurement of the absorbance values of said reconstituted dye solutions using a vertical photometer will give an indication of calibration of the vertical photometer and measurement of the absorbance values of said separate vessels will give an indication of the linearity of said vertical photometer.

* * * * *